US006181319B1

(12) United States Patent
Fujita et al.

(10) Patent No.: US 6,181,319 B1
(45) Date of Patent: Jan. 30, 2001

(54) METHOD OF DISPLAYING A SCATTERGRAM

(75) Inventors: Kyozo Fujita, Akashi; Kazuyuki Kanai, Kasai; Shigehiro Numada, Kobe, all of (JP)

(73) Assignee: Sysmex Corporation, Kobe (JP)

( * ) Notice: Under 35 U.S.C. 154(b), the term of this patent shall be extended for 0 days.

(21) Appl. No.: 09/042,664

(22) Filed: Mar. 17, 1998

(30) Foreign Application Priority Data

Mar. 17, 1997 (JP) .................................................. 9-063303

(51) Int. Cl.[7] ........................................................ G09G 5/36
(52) U.S. Cl. ............................................. 345/134; 364/555
(58) Field of Search ................................... 345/440, 133, 345/134, 150; 382/128, 133, 134; 364/555

(56) References Cited

U.S. PATENT DOCUMENTS

| 5,137,809 | | 8/1992 | Loken et al. ...................... 437/7.21 |
| 5,532,943 | * | 7/1996 | Asano et al. ......................... 364/555 |
| 5,605,805 | * | 2/1997 | Verwer et al. ....................... 435/7.24 |
| 5,824,269 | * | 10/1998 | Kosaka et al. ........................... 422/73 |
| 5,945,293 | * | 8/1999 | Siiman et al. ....................... 435/7.24 |
| 5,959,607 | * | 9/1999 | Montijo ................................ 345/134 |

FOREIGN PATENT DOCUMENTS 3-131756 * 6/1991 (JP) .

* cited by examiner

Primary Examiner—Richard A. Hjerpe
Assistant Examiner—Kevin M. Nguyen

(57) ABSTRACT

A method of displaying a scattergram includes measuring a plurality of particles with a particle measuring apparatus and preparing distribution data representing a frequency distribution of the particles on a two-dimensional coordinate plane based on a pair of parameters obtained from each of the particles. Thereafter, a scattergram is displayed based on the distribution data on a color display device by allowing the coordinates of a particle to correspond to a pixel, each of the pixels being made of three fundamental color luminescent components. A luminance of each of the three fundamental color luminescent components corresponds to a frequency of the particles on the scattergram. As such, the frequencies of the particles are displayed in different colors.

25 Claims, 5 Drawing Sheets

METHOD OF DISPLAYING A SCATTERGRAM

CROSS-REFERENCES TO RELATED APPLICATIONS

This application is related to Japanese Patent Application No. HEI 9-63303 filed on Mar. 17, 1997 whose priority is claimed under 35 USC §119, the disclosure of which is incorporated herein by reference in its entirety.

BACKGROUND OF THE INVENTION

1. Field of the Invention

The present invention relates to a method of displaying a scattergram. More particularly, the present invention relates to a method of displaying a two-dimensional distribution of particles measured by a particle measuring apparatus.

2. Description of the Related Arts

Heretofore, there is known a method or apparatus for measuring a plurality of particles by a particle measuring apparatus, preparing a two-dimensional scattergram showing a particle distribution on the basis of parameters obtained from each of the particles, classifying the particles on the scattergram into, for example, a leukocyte group, erythrocyte group and epithelial cell group, and displaying the groups in different colors.

Also, a method or apparatus is known in which particles on a two-dimensional scattergram are displayed for classification by means of contour lines (See, for example, U.S. Pat. No. 5,137,809).

However, such conventional methods raise a problem that it is difficult to grasp the quantitative characteristics of the particles from the scattergram because the frequency information is not clearly displayed on the scattergram.

SUMMARY OF THE INVENTION

The present invention has been made in view of these circumstances and the purpose thereof is to provide a method in which the information from the scattergram is easy to grasp by displaying with different colors the frequencies of the particles distributed on the scattergram.

Accordingly, the present invention provides a method of displaying a scattergram, comprising the steps of: measuring a plurality of particles with a particle measuring apparatus; preparing distribution data representing a frequency distribution of the particles on a two-dimensional coordinate plane based on a pair of parameters obtained from each of the particles; displaying a scattergram based on the distribution data on a color display device having pixels by allowing the coordinates of a particle to correspond to a pixel, each of the pixels being made of three fundamental color luminescent components; allowing a luminance of each of the three fundamental color luminescent components to correspond to a frequency of the particles on the scattergram; and displaying the frequencies of the particles in different colors.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

Figure 1:
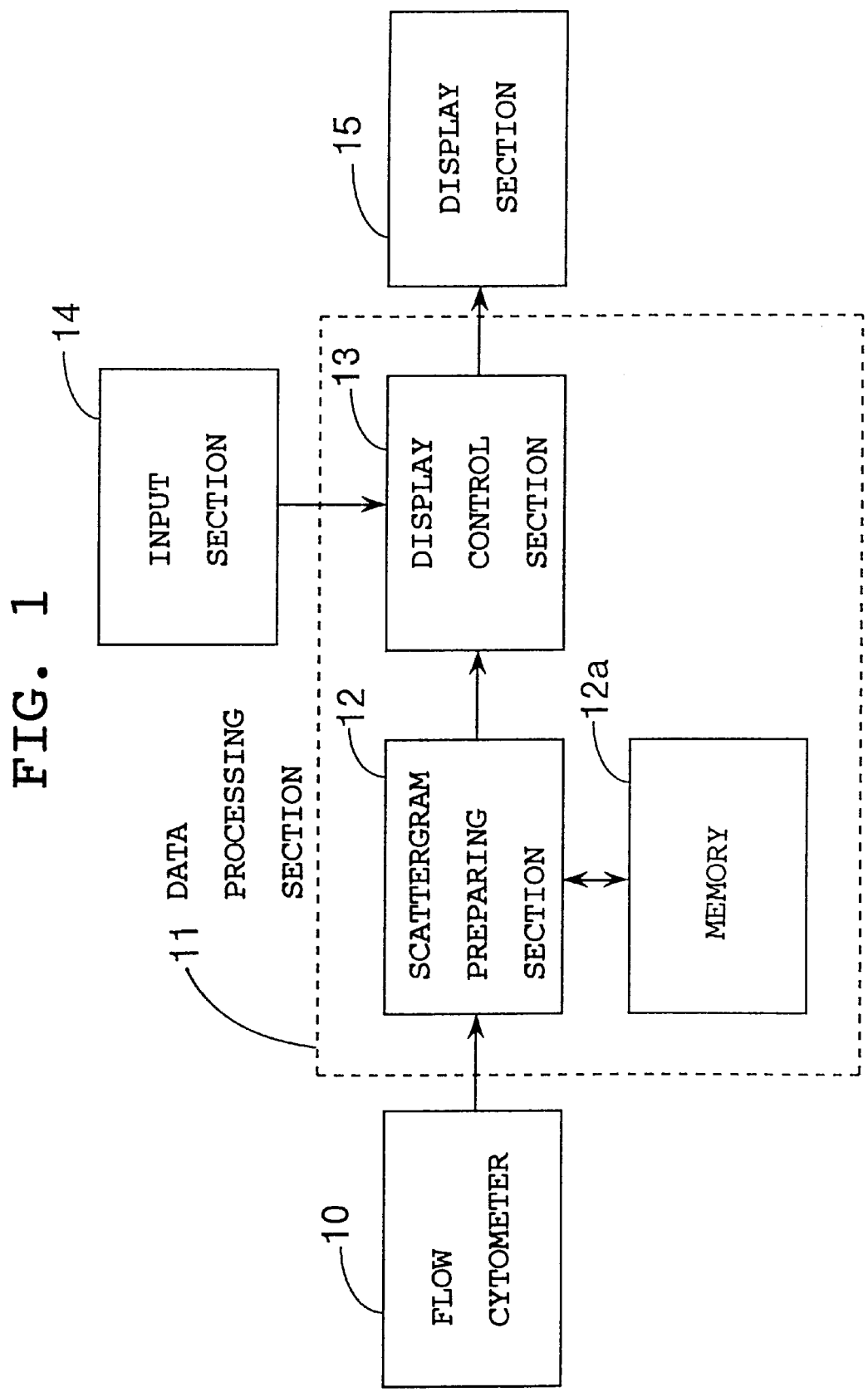
FIG. 1 is a block diagram of a particle measuring apparatus to be used according to an embodiment of the present invention.

The particle measuring apparatus to be used in the present invention may be any apparatus which can measure a plurality of particles to obtain a parameter representing the characteristics of each particle. Such as apparatus can include, for example, a flow cytometer for optically obtaining at least one parameter of a particle flowing through a sheath flow cell; or an electrical detecting apparatus which can electrically detect a change in impedance of an orifice in an electrolytic solution when a particle passes through the orifice.

The plurality of particles to be measured by the particle measuring apparatus are not specifically limited but may be, for example, erythrocytes, leukocytes, epithelial cells and other solid objects which are contained in body fluids of a mammalian animal including a human being, for example blood or urine.

The pair of parameters obtained from each particle may be parameters representing characteristics of the particle measured by the particle measuring apparatus. If the particle measuring apparatus is a flow cytometer, these parameters are, for example, a forward scattered light intensity and a fluorescent light intensity. In an electrical detecting device, the parameters are, for example, changes in impedances with respect to a direct current and a high frequency current.

The distribution data representing a frequency distribution of particles on a two-dimensional coordinate plane may be a set of data of coordinates and frequencies obtained by plotting each particle on the coordinate plane having orthogonal coordinate axes with the pair of parameters represented by the axis of ordinate and the axis of abscissa.

Further, the color display device to be used in the present invention may include pixels constituting the display screen, and each of the pixels includes luminescent components in three fundamental colors for full color display, namely, in red (R), green (G), and blue (B). The color display device may be a CRT, an LCD, or a PDP for full color display.

By allowing the frequency of particles on the scattergram to correspond to the luminance of each of the three fundamental color luminescent components, it is meant that, when particles are plotted on a single point having the same coordinates on the distribution data, the pixel corresponding to the coordinates is allowed to emit light with a color corresponding to the number of plotting times (frequency). Thereby, the frequency of particles distributed on the scattergram is displayed in different colors.

To allow the frequency of particles to correspond to the luminance of each of the three fundamental color luminescent components is, for example, to display the maximum frequency by red, the minimum frequency by blue, and the intermediate frequencies by the intermediate colors such as yellow, turquoise, and the like. Namely, the frequency of particles is displayed so as to correspond to, for example, the wavelength of a color by determining the luminance of each of the three fundamental color (R, G, B) luminescent components constituting the pixel.

In this case, therefore, it is preferable that, among the three luminescent components constituting the pixel corresponding to the maximum frequency, the red (R) luminescent component has the maximum luminance, and the green and blue (G, B) luminescent components each have the minimum luminance.

Alternatively, an arbitrary frequency may be set beforehand, and the luminances of all the three fundamental color luminescent components for the pixel corresponding to a frequency larger than the set frequency may be equal, whereby the pixel is displayed in white (or gray, black). This allows the region of particles having a frequency larger than the set frequency to be displayed in white, so that it is possible to find a cross section (contour line) of the frequency distribution by automatically or manually changing the set frequency successively.

EMBODIMENTS

Preferable embodiments of the present invention are now detailed with reference to the attached drawings. However, these embodiments and the drawings are not intended to limit the scope of the present invention.

FIG. 1 is a block diagram showing a construction of a particle analyzing apparatus according to the present invention. A flow cytometer 10 serves to measure a specimen pretreated for measurement, such as a specimen in which the blood cells are suspended as particles by dilution/hemolysis treatment of a human blood.

The flow cytometer 10 detects two kinds of signals, namely the forward scattered light intensity and the fluorescent light intensity every time a particle passes through a sheath flow cell incorporated in the flow cytometer 10. The detected signals are supplied to a data processing section 11 as parameters representing the characteristics of the particle. In the data processing section 11, a scattergram preparing section 12 prepares two-dimensional distribution data in the memory 12a by plotting the two parameters, namely the fluorescent light intensity and the forward scattered light intensity, on the X-axis and the Y-axis, respectively.

Figure 2:
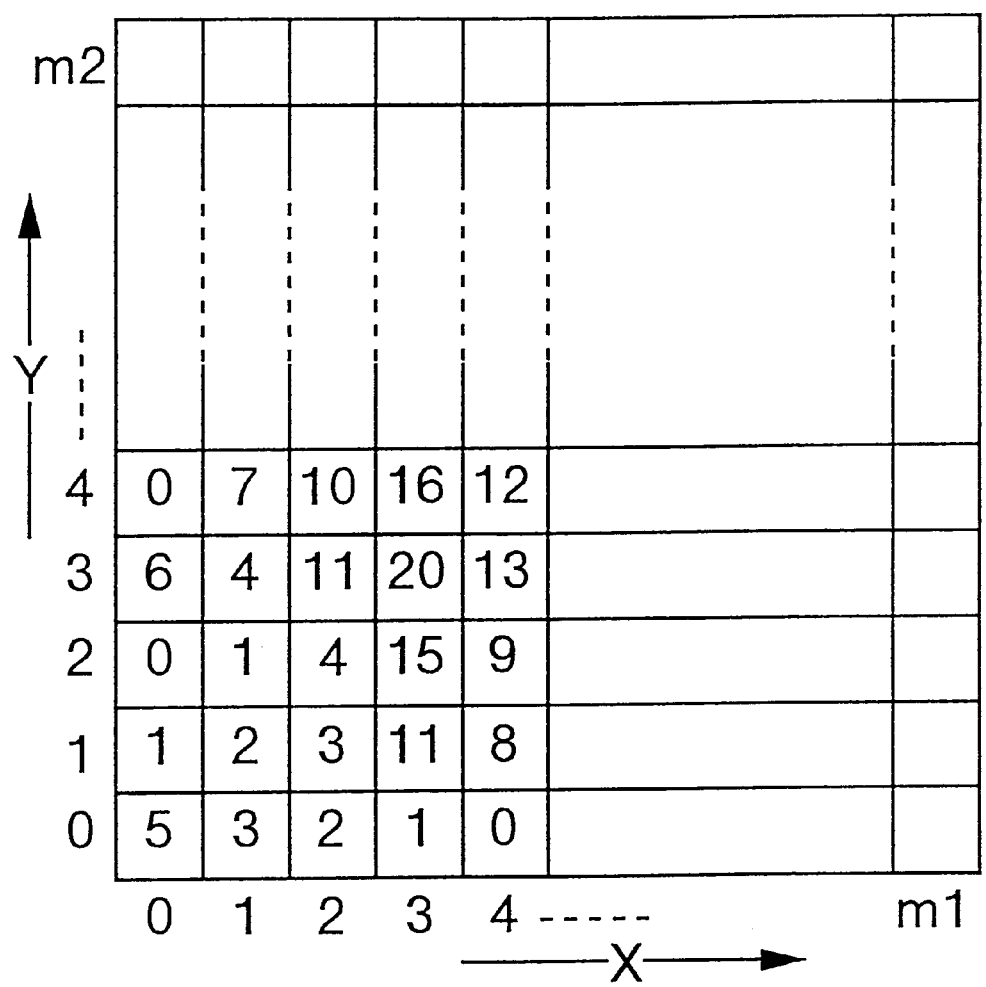
FIG. 2 is an explanatory view showing distribution data to be used according to the embodiment of the present invention.

Referring to FIG. 2, the memory 12a includes a memory region having a parameter X separated into (m1+1) channels (ranks) (from 0 to m1) and a parameter Y separated into (m2+1) channels (ranks) (from 0 to m2). Thus, the memory region is divided into (m1+1)×(m2+1) basic memory elements.

Every time the signals X and Y are inputted, the scattergram preparing section 12 increments data in the basic memory element at an address corresponding to the magnitudes of X and Y thus inputted.

When the signals X and Y for all the particles have been inputted into the scattergram preparing section, the distribution data are completed. FIG. 2 shows an example of the distribution data in which the particles having the parameter X equal to 3 and the parameter Y equal to 2 are 15 in number among the total particles, namely, the frequency of these particles is 15.

The distribution data thus prepared are processed by the display control section 13 under a condition inputted from the input section 14 and are displayed as a two-dimensional scattergram in color on a display section 15 (full color CRT). The data processing section 11 is constructed with a personal computer, and the input section is constructed with a keyboard or a mouse.

The process performed in the display control section 13 is now explained.

When the operator selects an "automatic operation mode" in the input section 14, the display control section 13 reads out the distribution data (FIG. 2) from the memory 12a and automatically retrieves (searches for) the maximum value of the data in the basic memory elements. Upon finding that the maximum value (maximum frequency) is P, the display control section 13 sets the relation as shown in FIG. 3 between the frequency and the luminance (R, G, B) of the three fundamental color luminescent components constituting each of the pixels when a one-to-one correspondence is established between the basic memory elements and the pixels on the display section 15.

By this relationship, the luminances (R, G, B) of the three fundamental color luminescent components in each pixel will be (255, 0, 0) when the pixel corresponds to a frequency of P; (255, 255, 0) when it corresponds to a frequency of 3P/4; (0, 255, 0) when it corresponds to a frequency of P/2; (0, 255, 255) when it corresponds to a frequency of P/4; and (0, 0, 255) when it corresponds to a frequency of 0, whereby the pixels display the colors red-yellow-green-turquoise-blue in accordance with the frequencies P to 0.

Figure 3:
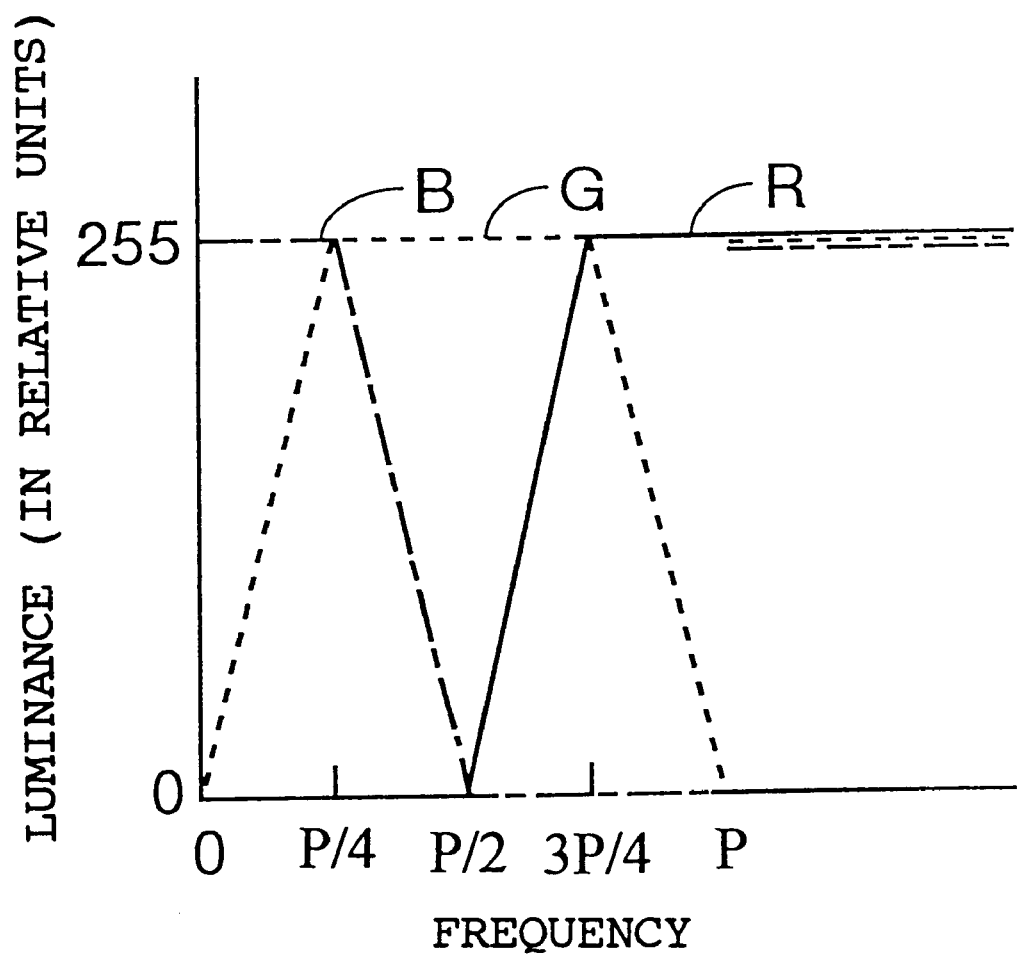
FIG. 3 is a graph showing a frequency-luminance relation according to the embodiment of the present invention.
Figure 4:
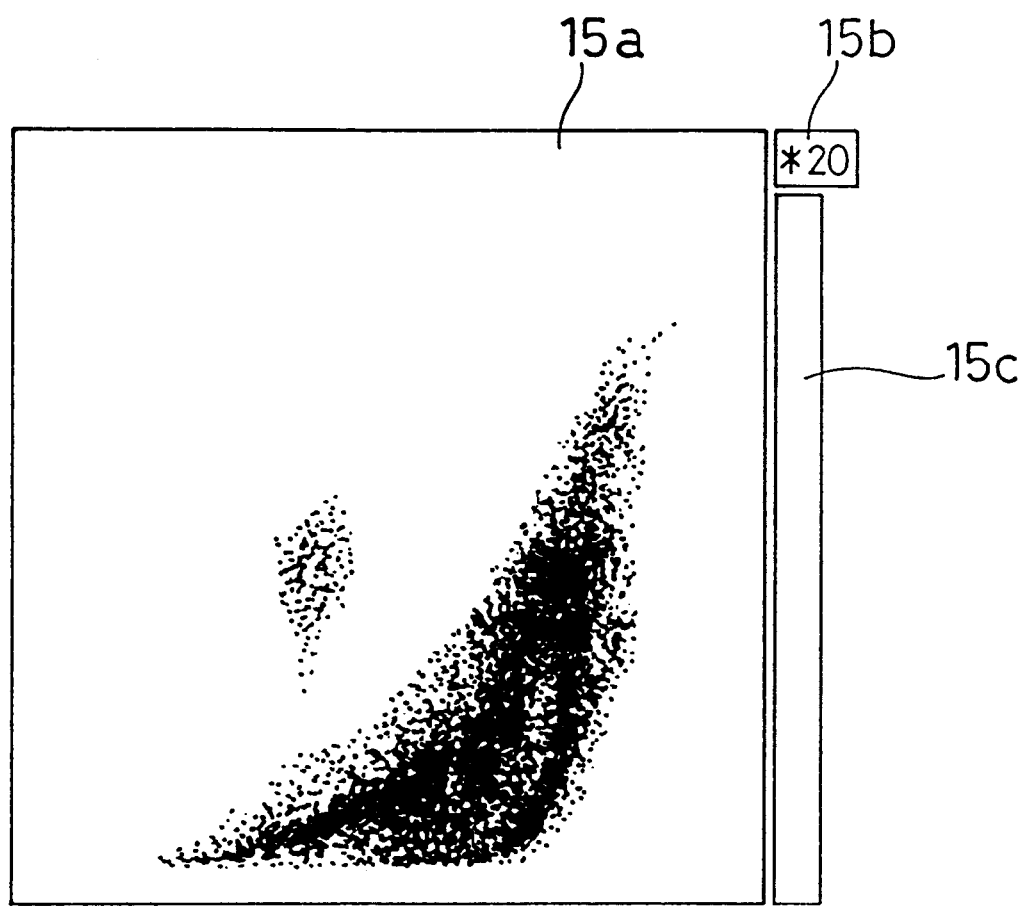
FIG. 4 is an explanatory view showing an exemplary display according to the embodiment of the present invention.

Thus, the display control section 13 displays the two-dimensional scattergram corresponding to the distribution data of FIG. 2 in color on the scattergram display region 15a of the display section 15 with the axis of abscissa representing the fluorescent light intensity and the axis of ordinate representing the forward scattered light intensity, as shown in FIG. 4. Also, the display control section 13 displays the retrieved maximum frequency P (here, 20) on the frequency display region 15b. The asterisk symbol "*" displayed on the frequency display region 15b indicates that the frequency "20" is the maximum frequency obtained by the automatic retrieval. The display control section 13 also displays a color bar 15C on the display section 15 as a scale showing a correlation between the frequencies and the colors shown in FIG. 3.

On the other hand, when the operator selects a "manual operation mode" and inputs the frequency of, for example, 10 as the maximum frequency P in the input section 14, the display control section 13 sets the relationship between the frequencies and the luminances (R, G, B) of the three fundamental color luminescent components constituting each of the pixels with respect to the distribution data (FIG. 2) with the maximum frequency being P=10, as shown in FIG. 3. At the same time, the luminances (R, G, B) of the three fundamental color luminescent components of all the pixels corresponding to frequencies of more than 10 are set to be (255, 255, 255).

By this relationship, the pixels display the colors red-yellow-green-turquoise-blue in accordance with the frequencies from 10 to 0, and display white in accordance with the frequencies of more than 10.

Figure 5:
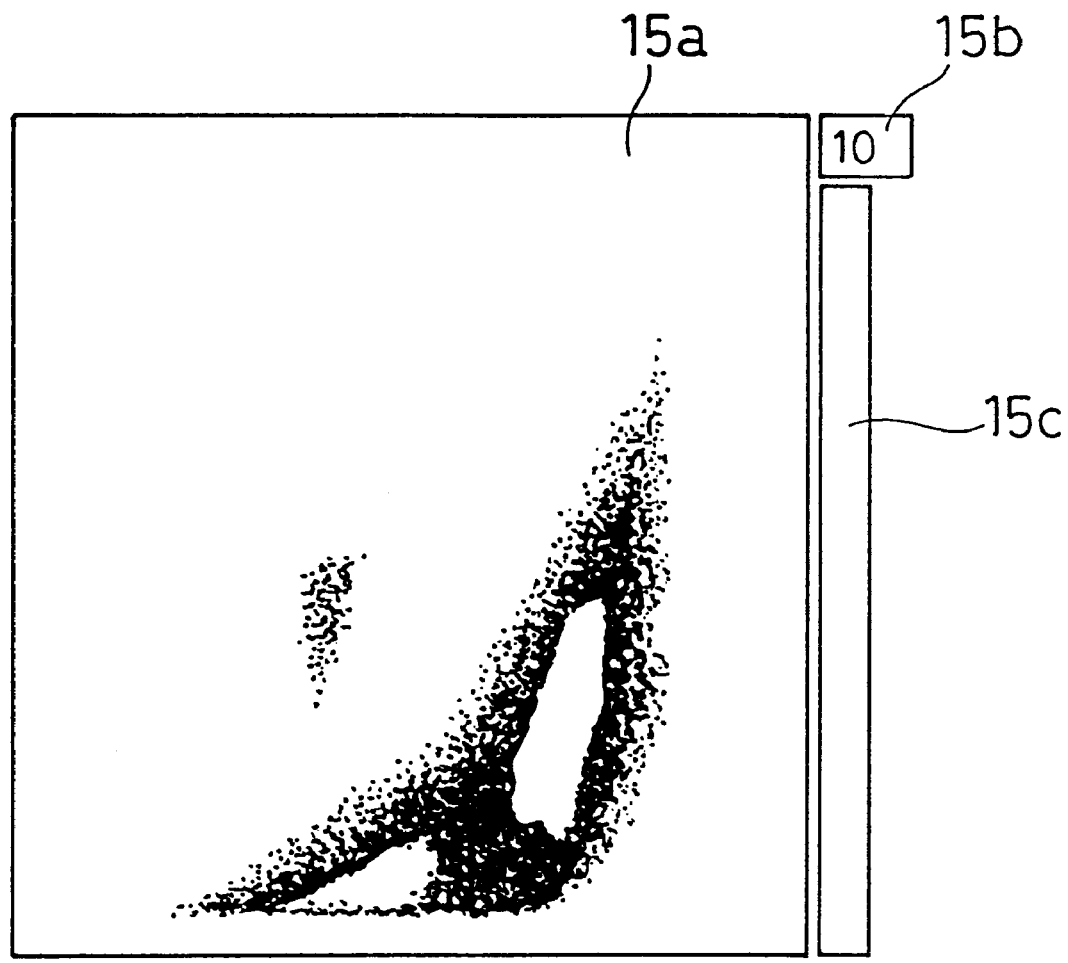
FIG. 5 is an explanatory view showing another exemplary display according to the embodiment of the present invention

Thus, the display control section 13 displays the two-dimensional scattergram corresponding to the distribution data of FIG. 2 in color on the scattergram display region 15a of the display section 15, as shown in FIG. 5. Also, the display control section 13 displays the inputted maximum frequency P (here, 10) on the frequency display region 15b. The display control section 13 also displays a color bar 15C on the display section 15 as a scale showing a correlation between the frequencies and the colors shown in FIG. 3.

Accordingly, when the operator arbitrarily changes the maximum frequency P in the "manual operation mode", the frequency displayed on the frequency display region 15b changes in accordance therewith, whereby the colors of the pixels corresponding to the frequencies P to 0 in the two-dimensional scattergram change and the white area changes. Alternatively, the maximum frequency P to be inputted may be automatically increased or decreased.

According to this embodiment, since the frequencies in the two-dimensional scattergram are displayed in different colors in the "automatic operation mode", the operator can intuitively perform a quantitative comparison of the particle groups on the scattergram and also confirm the classification of particle groups on the screen.

Further, when the operator inputs an arbitrary frequency in the "manual operation mode", the pixels having frequencies larger than the inputted frequency are displayed in white, with the contour line of the frequency being represented by an outline of the white region, so that the operator can recognize the frequency distribution more accurately.

According to the present invention, the operator can analyze the characteristics of the particles to be measured more clearly, since the frequencies of particles distributed on the scattergram are displayed in different colors and the distribution information is provided together with the frequency information.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What we claim is:

1. A method of displaying a scattergram, comprising the steps of:
   measuring a plurality of particles with a particle measuring apparatus;
   preparing distribution data representing a frequency distribution of the particles on a coordinate plane based on a pair of parameters obtained from the measurements of the particles;
   displaying a scattergram based on the distribution data on a color display device, wherein coordinates of a particle correspond to a pixel;
   controlling colors of the color display device to correspond to frequency of occurrence of the parameter pairs of the particles on the scattergram based on a function representative of a relationship between the frequency of occurrence of the parameter pairs and the colors, and
   displaying the frequencies of occurrence of the parameter pairs of the particles in different colors.

2. A method of displaying a scattergram according to claim 1 wherein the particles to be measured include blood cells of body fluids of a human being.

3. A method of displaying a scattergram according to claim 1 wherein the particle measuring apparatus is a flow cytometer and the pair of parameters include a scattered light intensity and a fluorescent light intensity obtained from the plurality of particles.

4. A method of displaying a scattergram according to claim 1 wherein, when a pixel corresponds to a maximum frequency of occurrence of the distribution data, a luminance of at least one of three color components of the pixel is set at a maximum luminance.

5. A method of displaying a scattergram according to claim 1 further comprising the step of setting an arbitrary frequency of occurrence range and, for pixels corresponding to the frequencies of occurrence outside of the set frequency of occurrence range, displaying them in the same color.

6. A method of displaying a scattergram according to claim 1 further comprising the step of displaying a scale showing a correlation between the frequencies and the colors on the color display device together with the scattergram.

7. The method of claim 1, wherein each pixel includes three color luminescent components corresponding to frequencies of occurrence of the parameter pairs.

8. The method of claim 1, wherein each color corresponds to a frequency of occurrence range.

9. The method of claim 7, wherein each color corresponds to a frequency of occurrence range.

10. The method of claim 1, wherein the coordinate plane is a two-dimensional coordinate plane.

11. An apparatus, comprising:
    a measuring device, adapted to measure a plurality of particles;
    a data processing device, adapted to prepare distribution data representing a frequency distribution of the measured particles based on a pair of parameters obtained from the particle measurements; and
    a color display, adapted to display a scattergram based on the distribution data, wherein coordinates of a particle correspond to a pixel, colors of the display correspond to a frequency of occurrence of the parameter pairs of the particles of the scattergram based on a function representative of a relationship between the frequency of occurrence of the parameter pairs and the colors, and frequencies of occurrence of the parameter pairs of the particles are displayed in different colors.

12. The apparatus of claim 11, wherein the measuring device is a flow cytometer.

13. The apparatus of claim 12, wherein the flow cytometer measures parameters of the particles including scattered light intensity and fluorescent light intensity.

14. The apparatus of claim 11, wherein the data processing device includes a scattergram preparing section and a memory.

15. The apparatus of claim 14, wherein the data processing device further includes a display control section for controlling the color display.

16. The apparatus of claim 15, wherein the particles include blood cells.

17. The apparatus of claim 11, wherein each color corresponds to a range of frequencies of occurrence.

18. The apparatus of claim 11, wherein a maximum frequency of occurrence is displayed in red, a minimum frequency of occurrence is displayed in blue and intermediate frequencies of occurrence are displayed as intermediate colors.

19. The apparatus of claim 11, wherein each pixel includes three color luminescent components corresponding to frequencies of occurrence of the parameter pairs.

20. The apparatus of claim 11, wherein the color display displays the scattergram in a two-dimensional coordinate plane.

21. The apparatus of claim 14, wherein the memory stores information of the particles based on a value of pairs of parameters measured.

22. The apparatus of claim 21, wherein the frequency of occurrence represents parameter pair values of the particles.

23. The method of claim 7, wherein the step of controlling includes changing luminance of each color luminescent component based on a function representing changing luminance corresponding to changing frequency of occurrence of the parameter pairs.

24. The method of claim 1, wherein a maximum frequency of occurrence is displayed in red, a minimum frequency of occurrence is displayed in blue and intermediate frequencies of occurrence are displayed as intermediate colors.

25. The apparatus of claim 19, wherein the display is adapted to change luminance of each color luminescent component based on a function representing changing luminance corresponding to changing frequency of occurrence of the parameter pairs.

* * * * *